United States Patent [19]

Smith

[11] Patent Number: 5,374,074
[45] Date of Patent: Dec. 20, 1994

[54] APPARATUS FOR ATTACHING INTRAVENOUS INFUSION POLES TO FOLDABLE WHEELCHAIRS

[76] Inventor: Sidney Smith, 1320 11th Ave. South, Apt. 2, Birmingham, Ala. 35205

[21] Appl. No.: 81,142

[22] Filed: Jun. 25, 1999

[51] Int. Cl.⁵ ............................................. A47C 7/62
[52] U.S. Cl. ........................... 280/304.1; 297/DIG. 4
[58] Field of Search ................. 280/304.1, 293, 250.1, 280/292; 248/122; 180/907; 297/188, 191, 194, DIG. 4; 5/503.1, 658; 292/247; 24/270, 273, 20 S, 330; 440/102

[56] References Cited

U.S. PATENT DOCUMENTS

| | | | |
|---|---|---|---|
| 991,192 | 5/1911 | Battenfeld | 24/270 |
| 3,709,556 | 1/1973 | Allard et al. | 297/188 |
| 4,511,157 | 4/1985 | Wilt, Jr. | 280/304.1 |
| 4,511,158 | 4/1985 | Varga et al. | 280/292 |
| 4,572,536 | 2/1986 | Doughty | 280/304.1 |
| 4,605,378 | 8/1986 | Hamilton | 440/102 |
| 4,767,131 | 8/1988 | Springer et al. | 297/188 X |
| 4,840,391 | 6/1989 | Schneider | 280/304.1 |
| 5,083,807 | 1/1992 | Bobb et al. | 280/304.1 |
| 5,180,181 | 1/1993 | Letechipia | 297/DIG. 4 |
| 5,219,139 | 6/1993 | Hertzler et al. | 280/304.1 X |
| 5,236,213 | 8/1993 | Trickett | 280/304.1 |

Primary Examiner—Brian L. Johnson
Assistant Examiner—F. Zeender
Attorney, Agent, or Firm—Veal & Associates

[57] ABSTRACT

A coupling device for connecting a mobile medical apparatus such as a wheeled support stand for intravenous infusion devices to a wheelchair. The coupling device attaches to the framework at the rear of said wheelchair and is adjustable between an inward storage position and an outward operational position. A variable clamping means secures support stands, of various dimensions, to the rear of the wheelchair for tandem movement with said wheelchair.

7 Claims, 3 Drawing Sheets

APPARATUS FOR ATTACHING INTRAVENOUS INFUSION POLES TO FOLDABLE WHEELCHAIRS

FIELD OF THE INVENTION

The present invention generally relates to an apparatus for attaching a mobile intravenous (I.V.) stand to wheeled patient transporters, such as gurneys. More particularly, the present invention relates to an adjustable coupling device which connects at one end to the lower framework of a wheelchair while a remaining end utilizes an adjustable clamping device to secure mobile I.V. stands of various dimensions for concurrent movement with the wheelchair.

BACKGROUND OF THE INVENTION

The uninterrupted intravenous treatment of a patient under transport is vital for dependable patient health. Devices used for such treatment devices often take the form of intravenous infusion devices or pumps, hereinafter referred to as I.V.'s, which are supported on stands with wheels for mobility. These mobile I.V. stands must be in close proximity with a patient traveling on a wheeled transport such as a wheelchair. Today, the mobile I.V. stand requires personnel to guide the I.V. stand while additional personnel move the wheelchair with the patient. On occasion, the patient guides the I.V. stand while an attendant pushes the wheelchair. Often, the patient is physically unable to guide the mobile I.V. stand and the attendant must maneuver both the I.V. stand and the wheelchair. Thus, the attendant's attention is diverted the primary responsibility of transporting the patient to guiding the mobile I.V. stand or similar mobile instrument. Problems exist when transporting the patient and mobile I.V. stands over uneven surfaces found in doorways, elevators and the like. Although the wheelchair may be adapted for movement over such uneven surfaces, many of the mobile I.V. stands are not so adaptable as they often have caster wheels of a smaller diameter. Often, the entire I.V. stand must be raised by the attendant while simultaneously moving the wheelchair over a surface obstruction.

Several techniques are currently used for rigidly affixing a mobile I.V. stand to wheeled transport devices such as wheelchairs. A device disclosed in U.S. Pat. No. 4,840,391 issued to Schneider teaches a mobile I.V. stand coupled to the upper frame of a wheelchair. The mobile I.V. stand is pushed ahead and to the side of the wheelchair or transporting device. This type of coupling creates a larger, wider, and unstable unit that is more difficult to maneuver through narrow doorways, aisles and the like. Another disadvantage is that when an uneven surface is encountered, the chair must be tipped backward to raise the coupled mobile I.V. stand. This tipping is burdensome, depending on the size of the stand, and could increase the risk of injury to the patient under transport. The coupling device in Schneider also interferes with the access to and from the wheelchair due to the position of the adjusting member.

Another coupling mechanism is of the type disclosed in U.S. Pat. No. 5,083,807 issued to Bobb et al on Jan. 28, 1992. This coupling method uses clamps to attach the mobile I.V. stand to the front footrests of a wheelchair. The same problems of maneuverability, stability and access to the chair are found in this invention as were present in Schneider.

The coupling mechanism of U.S. Pat. No. 4,767,131 has a mounting clamp which attaches to the rear of a wheelchair. This mounting clamp positions a mobile I.V. stand directly behind the attendant thereby impeding the attendant's gait. This device increases the risk of the operator tripping or falling at his or her own peril as well as risking injury to the patient under transport. Additionally, with the attachment of the device to the lateral frame of the wheelchair and height above the ground instability is associated with this transporting device.

U.S. Pat. No. 4,511,158 issued to Varga et al teaches a device for attaching an I.V. pole to a wheeled stretcher or other wheeled patient transport. This device contemplates the use of extensive support hardware such as brackets and suggests welding this hardware in place. Varga does not contemplate the use of existing support structures specific to a wheelchair design such as the coaligned apertures of the lower frame members. The traction clamp utilized by Varga may be limited in it's ability to engage I.V. posts having a wide variety of diameters.

There is a need for a coupling device which attaches to a wheelchair frame which allows secure coupling with I.V. poles and when not coupled the device will not interfere with wheelchair use. The device should use only existing wheelchair frame with no modifications, attach to any size or shape I.V. pole without modifications, allow stability of patient and I.V. pole tandem movements, and allow simple and quick coupling and retracting mechanisms. The mobile I.V. stand can best be maneuvered by an attendant when trailing immediately behind the wheelchair such that the I.V. stand is between the attendant at the back of the wheelchair. The coupling device needs to be attached to the frame of the wheelchair in a semipermanent manner and yet allows a normal folding of the wheelchair. The coupling device needs to be adjustable to a position that will not interfere with the operation of the wheelchair when no mobile stand is connected for use. The coupling device and attached mobile I.V. stand must be maneuverable over a variety of uneven surfaces with no tilting and lifting of the I.V. stand and chair.

SUMMARY OF THE INVENTION

With the foregoing in mind it is an object of this invention to provide a coupling device for connecting a mobile I.V. stand or similar wheel and pole medical apparatus to a wheelchair.

Another object of this invention is to provide an adjustable coupling device that can be simply and easily attached to any wheelchair in a semipermanent manner with no structural modifications.

Yet another object of the present invention is to provide a coupling device which allows safe maneuverability of a wheelchair and mobile I.V. by attaching to the lower frame work of the wheelchair and lower aspect of the I.V. pole.

Still a further object of the present invention is to provide a coupling device that will secure I.V. devices of varying sizes and dimensions to a wheelchair.

Still, another object is to provide a simple and durable attachment device which is easily installed and simple to work.

These and other objects of the present invention are accomplished through the use of a telescoping coupling device. This telescoping coupling device is affixed to a universal joint of cross members of the frame of the wheelchair with a threaded bolt. The telescoping coupling device adjusts between an extended operational position and an inward storage position. An adjustable clamping means secures upright mobile I.V. stands of varied diameters and dimensions to the wheelchair for tandem movement with the wheelchair.

DETAILED DESCRIPTION OF THE PREFERRED EMBODIMENT

Figure 1:
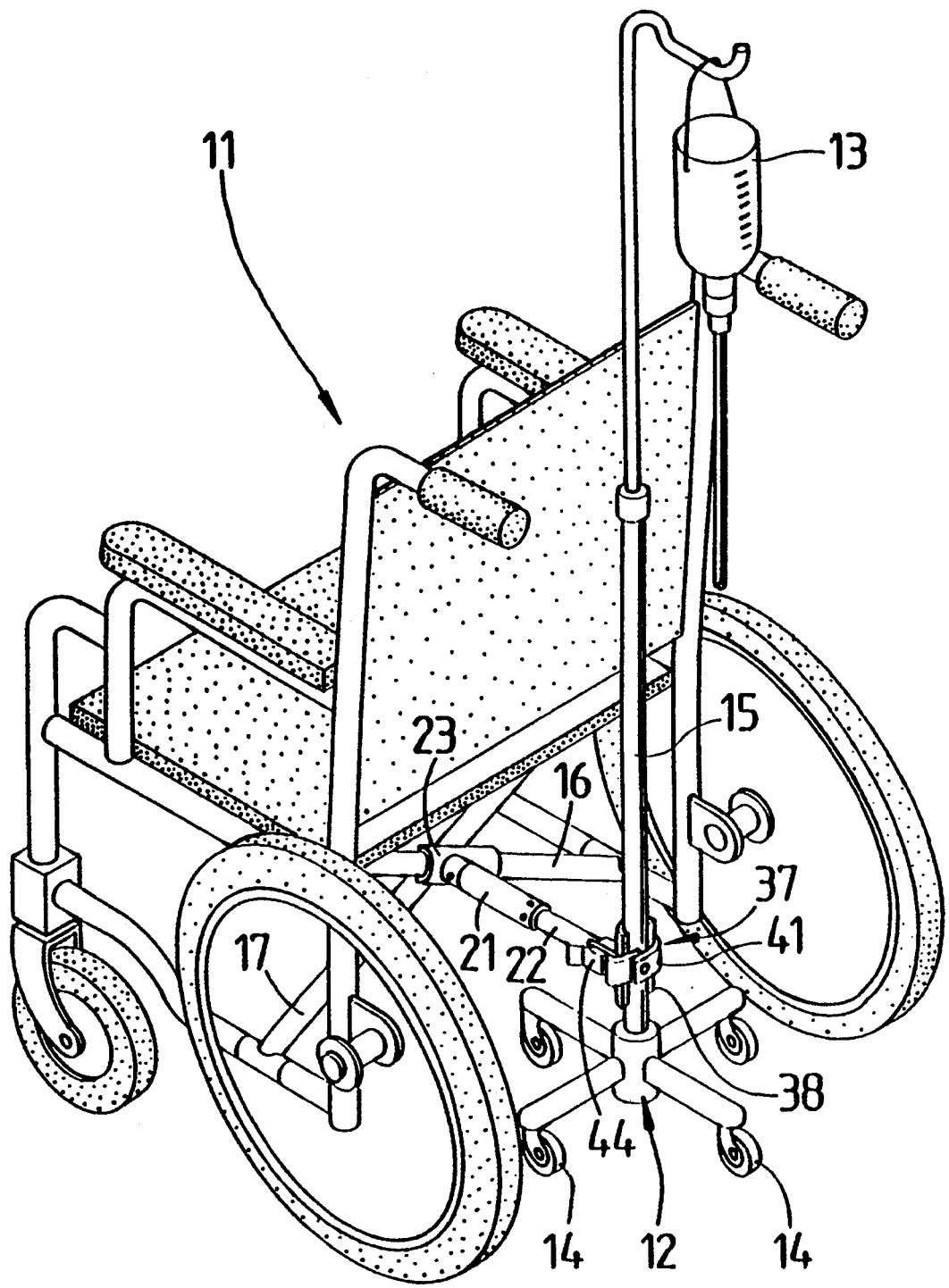
FIG. 1 is a perspective view of the coupling device connecting a wheelchair and a mobile I.V.

Referring to the drawings for clearer understanding of the invention, there can be seen in FIG. 1 a wheelchair 11 and an upright mobile I.V. stand 12. The I.V. stand 12 carries an I.V. pump or bag 13 and is supported by a plurality of wheels 14. An upright tubular member 15 of variable diameter and dimensions carries the pump or bag 13 of I.V. stand 12. The diameter or dimensions of the tubular member 15 varies with the size of the pump or bag 13 it supports as well as differing among manufactures of the I.V. stand 12.

The wheelchair 11 has as part of its frame tubular cross members 16 and 17 which cross at a junction 18 and have coaligned apertures 20 at this junction 18. A fastener is normally inserted through the coaligned apertures 20 of cross members 16 and 17 to provide stability, support and folding nature of wheelchair 11. A coupling device 19 connects the I.V. stand 12 to cross members 16 and 17 of wheelchair 11 at junction 18.

Figure 4:
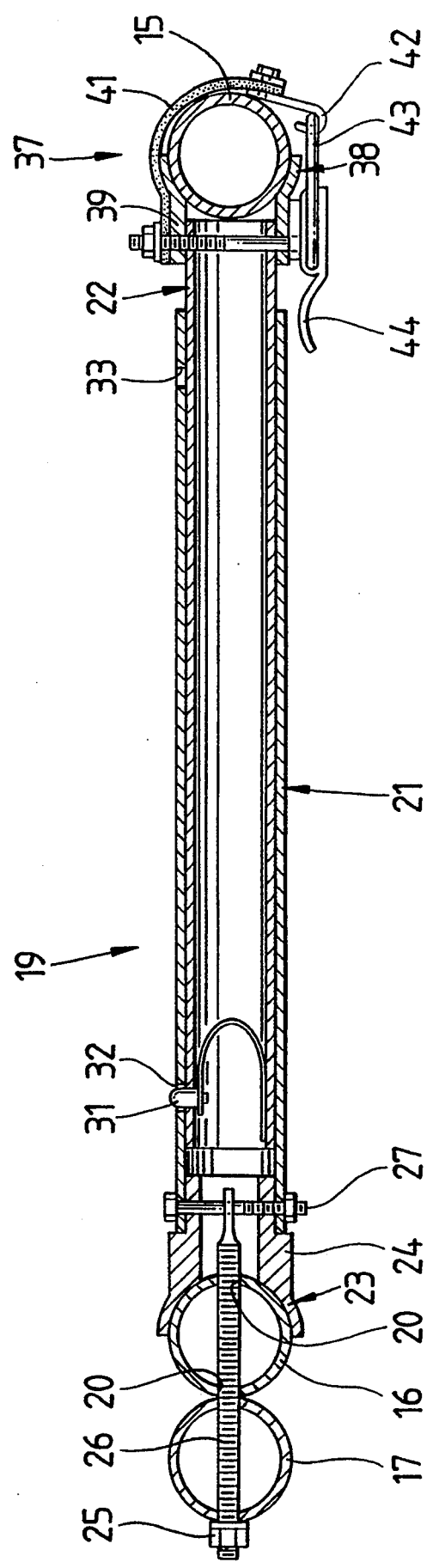
FIG. 4 is a longitudinal cross section of the coupling device.

The coupling 19 includes a first tubular member 21 having affixed at an end thereof a tubular boss 24 of a first semicylindrical guide 23. First semicylindrical guide 23 is adapted to mate with either tubular cross member 16 or 17 at the junction 16. A fastener 26 is affixed to the first tubular member and in any number of ways. In the described embodiment a cross bolt 27 extends through first tubular member 21 and fastener 26. The fastener 26 is inserted through aligned apertures 20 of cross members 16 and 17 as the first semicylindrical guide 23 is brought into engagement with cross member 16. A nut 25 secures fastener 26 and semicylindrical guide 23 to cross member 16 of wheelchair 11 as shown in FIG. 4.

The first tubular member 21 extends horizontally from the wheelchair 11 proximal said first semicylindrical guide 23. A second set of apertures 33 and 36 are formed through a wall of the first tubular member 21.

A second tubular member 22 slidably engages an end of said first tubular member 21 distal said wheelchair 11 for movement between an inward and extended position. A pin 31 is resiliently mounted to an end of the second tubular member 22 proximal said first tubular member 21. The pin 31 engages aperture 32 or 33 to secure the second tubular member 21 in an inward or outward position. In the alternative, the second tubular member 22 can be rotated such that pin 31 engages aperture 36 at secured outward position.

Figure 3:
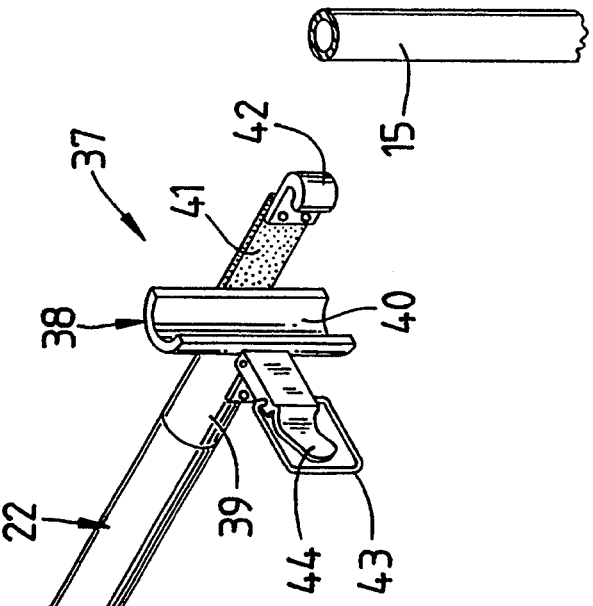
FIG. 3 is a perspective view of the clamping means of the coupling device.
Figure 2:
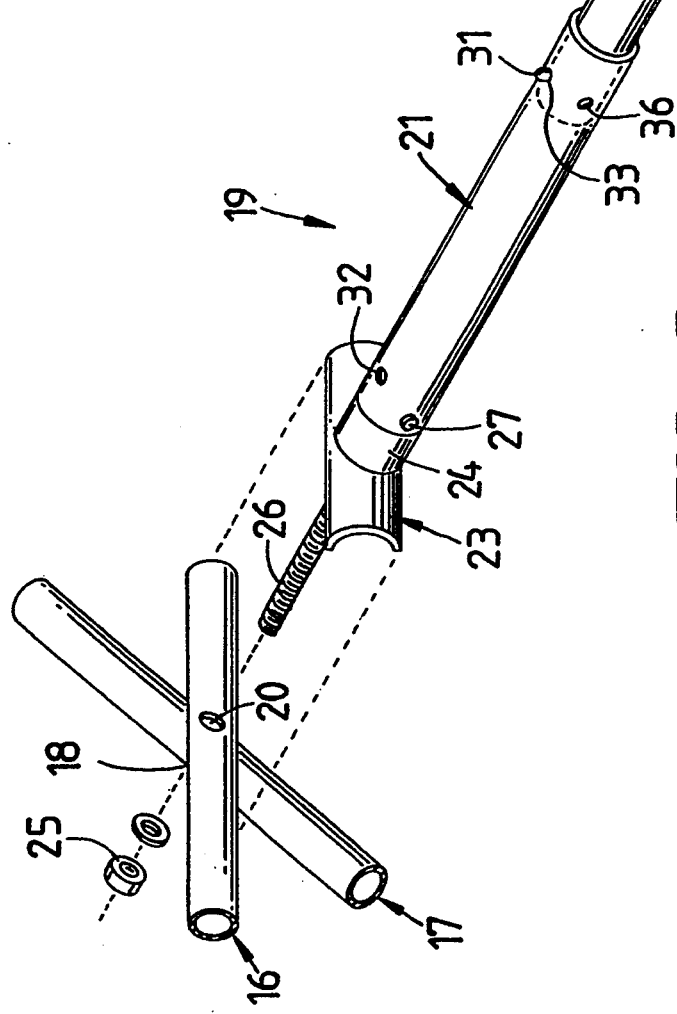
FIG. 2 is a perspective view of the coupling device.

Second tubular member 22 supports at an end distal the first tubular member 21 clamping means designated generally by reference numeral 37. In one embodiment the clamping means 37 includes a second semicylindrical guide 38 with a protruding tubular boss 39. The boss 39 is affixed to the distal end of the second tubular member 22. The second semicylindrical guide 38 is formed perpendicular to boss 39 as shown in FIG. 3. A concave face 40 of second semicylindrical guide 38 is adapted to engage the upright tubular member 15 of I.V. stand 12. A resilient strip 41 is affixed at one end to a distal end of said second tubular member 22 adjacent the second semicylindrical guide 38 and extends partially around the upright tubular member 15 of I.V. stand 12. This will also engage various other dimensions. Resilient strip 41 has attached to an end thereof a latch hook 42 which engages a latch bar member 43 pivotally mounted to a latch lever 44. The latch lever 44 is affixed to said second semicylindrical guide 38 and or second tubular portion 22 on a side opposite said strip 41. Latch hook 42 is engaged or disengaged from said latch bar member 43 by manual manipulation of latch lever 44. Thus the tubular member 15 of I.V. stand 12 is secured in mated abutment with face 40 of second semicylindrical guide 38 by latch lever 44.

In actual operation, the coupling device 19 is secured to wheelchair 11 as discussed hereinabove. The second tubular member 22 slides into the first tubular member 21 and is secured by pin 31 engaging aperture 32. In the inward position the second tubular member 22 is in close proximity with the rear of wheelchair 11 and does not interfere with operation of the wheelchair 11 without an attached I.V. stand 12.

When transporting a patient who requires an I.V. stand 12, the operator manually extends second tubular member relative to first tubular member 21. The pin 31 engages aperture 33 and secures the second tubular member 22 in an outward position relative to first tubular member 21. The face 40 of the second semicylindrical guide 38 must be oriented in a vertical position to engage upright tubular member 15 of the I.V. stand 12. Thus, the angle to which the first tubular member 21 is attached to cross members 16 or 17 will at times require that the second tubular member 22 be rotated and secured with the pin 31 engaging aperture 36 to insure that the second semicylindrical guide 38 is vertically oriented to conform with upright tubular member 15 of I.V. stand 12.

A clamping means 37 secures the tubular member 15 of I.V. stand 12 to the semicylindrical guide 38. One method of clamping includes an elastic strip 41 which engages a portion of the tubular member 15. The strip 41 has a latch hook 42 affixed to an end thereof which engages a pivotable latch bar member 43 of a latch lever 44 mounted to an opposite side of the second semicylindrical guide 38 or distal end of second tubular member 22. Other securing means, such as Velcro ® strips or metallic bands, may also be used in the embodiment. When secured, the I.V. pump 13 and stand 12 trail to the rear of the wheelchair 11 between the operator and the wheelchair 11. With the I.V. stand 12 in line with wheelchair 11 the unit is narrow and maneuverable about various obstacles. Additionally, because the I.V. poles is held between the wheelchair wheels and immediately behind the patient it does not interfere with the operator pushing wheelchair 11. The I.V. stand 12 raises and lowers with the rear of wheelchair 11 as the operator lifts or tilts the wheelchair 11 over obstructions. This gives the operator more control over the unit especially across uneven surfaces. The wheelchair 11 and secured I.V. stand 12 are moved through doorways, elevators and down ramps with as little lifting, tilting, or complex maneuvering as possible. Although I have shown my invention in one form, it will be obvious to those skilled in the art that it is not so limited but susceptible of various changes and modifications without departing from the spirit thereof.

What I claim is:

1. An apparatus for attaching a mobile medical apparatus to a foldable wheelchair such that said mobile medical apparatus and said foldable wheelchair are moved concomitantly, said apparatus comprising in combination:
    a) an elongated connecting member;
    b) means for mounting said connecting member to a lower frame member of said wheelchair including a first semicylindrical guide adapted for engagement with said frame member, said guide having formed medially thereon an orthogonally protruding tubular boss, said boss affixed to an end of said connecting member, and wherein said semicylindrical guide is secured for engagement with said frame member by a fastener which extends through an aperture in said frame member
    c) means for adjusting the length of said connecting member; and
    d) clamping means for securing said mobile medical apparatus at one end of said connecting member distal said means for mounting, such that said mobile medical apparatus is constrained to move directly behind and proximal said wheelchair.

2. An apparatus as defined in claim 1 wherein, said connecting member comprises a first tubular member which telescopically receives a second tubular member, said means for adjusting length secures said first and second tubular members relative to each other at a desired position of extension.

3. An apparatus as defined in claim 2 wherein said means for adjusting length comprises a pin resiliently mounted to said second tubular member and engagable within apertures in said first tubular member to secure said first and second tubular members in a desired position of extension.

4. An apparatus as defined in claim 3 wherein sets of apertures are defined through said first tubular member in offset angular relationship such that said second tubular member can be secured in a selected position rotated about the longitudinal axis of said connecting member to orient said clamping means with said mobile medical apparatus.

5. An apparatus as defined in claim 1 wherein said clamping means is an elastic strip fixed to said elongated connecting member at one end thereof, said elastic strip adapted to engage varied shaped stands of said mobile medical apparatus and having a fastening means attached.

6. An apparatus as defined in claim 5 wherein said fastening means is a latch and hook assembly.

7. An apparatus as defined in claim 2 wherein said second tubular member rotates within said first tubular member and a resilient pin mounted to said second tubular member selectively engages an aperture in said first tubular member such than an arcuate face of said semicylindrical guide is vertically oriented to engage a stand of said mobile medical apparatus.

* * * * *